United States Patent [19]

Babayan et al.

[11] Patent Number: 4,952,606
[45] Date of Patent: Aug. 28, 1990

[54] STRUCTURED LIPID CONTAINING DAIRY FAT

[75] Inventors: Vigen K. Babayan, Waban; George L. Blackburn, Jamaica Plain; Bruce R. Bistrian, Ispwich, all of Mass.

[73] Assignee: New England Deaconess Hospital Corporation, Boston, Mass.

[21] Appl. No.: 177,763

[22] Filed: Apr. 5, 1988

[51] Int. Cl.$^5$ ............................................. A61K 31/23
[52] U.S. Cl. .................................................. 514/552
[58] Field of Search ................. 514/557, 558, 560, 552

[56] References Cited

U.S. PATENT DOCUMENTS

| | | | |
|---|---|---|---|
| 3,232,971 | 2/1966 | Stein et al. | 260/410.7 |
| 3,450,819 | 6/1969 | Babayan et al. | 514/558 |
| 3,494,944 | 2/1970 | Seiden | 260/410.7 |
| 3,597,229 | 8/1971 | Mijinders et al. | 99/122 R |
| 4,087,564 | 5/1978 | Poot et al. | 426/603 |
| 4,423,072 | 12/1983 | Stahly | 514/552 |
| 4,521,440 | 6/1985 | Lansbergen | 426/602 |
| 4,528,197 | 7/1985 | Blackburn | 514/552 |
| 4,690,820 | 9/1987 | Simko | 514/904 |
| 4,753,963 | 6/1988 | Jandacek et al. | 514/560 |

FOREIGN PATENT DOCUMENTS 2097036  7/1970  France ................................ 514/560

OTHER PUBLICATIONS

*Handbook of Nonprescription Drugs*, 5th Ed., (1977), pp. 174–175.
"Bailey's Industrial Oil and Fat Products", Robert R. Allen et al., vol. 2, Fourth Edition, John Wiley & Sons.

*Primary Examiner*—Douglas W. Robinson
*Assistant Examiner*—Raymond J. Henley, III
*Attorney, Agent, or Firm*—Lahive & Cockfield

[57] ABSTRACT

The present invention features a transesterification product of a mixture of fatty acids and triglycerides which include dairy fat as a primary component. This composition shows unexpected benefits in nutritional applications either as a food or as an enteral or parenteral supplement. The method of nutritional support using this composition is also disclosed.

20 Claims, No Drawings

STRUCTURED LIPID CONTAINING DAIRY FAT

BACKGROUND OF THE INVENTION

The present invention relates to structured lipids and their nutritional value. Surprising and advantageous properties are obtained with transesterification products made from a mixture of fats or oils which include a dairy fat as one of its components.

Dairy fats, primarily cream, butter, and other dairy products, have long had an image of quality and good taste and, accordingly, these dairy products have been preferred ingredients for food consumption and cooking uses. In recent years, the use of these dairy products has been criticized because of health problems, e.g., the promotion of higher cholesterol and high density lipoprotein levels, associated with the consumption of these products. In addition, the cost of dairy products has increased greatly over the years.

Margarines have captured a place in the consumer market not only because they are cheaper than butter but also because their physical characteristics offer a more flexible route to insure good nutrition. For example, the linoleic acid needed to meet essential fatty acid requirements is easily added or used as one of the constituents of margarines. The margarine industry itself, however, has undergone a change in the last few years since the long-chain saturated fatty acids used in the past to form the margarines, particularlY the oleo margarines, have been found to be a problem in cases of hypercholesterolemia. Recent nutritional and medical studies have indicated that it is possible that a large amount of long-chain triglycerides in the diet may contribute to a greater onset of cancer, hypertension, and other major public health problems of civilized man.

Structured lipids and other transesterification products have been used for several years in the treatment of a variety of physical disorders. However, because of the studies showing a relationship between dairy products and elevated cholesterol levels, dairy products have been ignored as a source of fatty acids for structured lipids in the health care field.

Surprisingly, it has now been discovered that transesterification products made using dairy fat as one of the components have significant nutritional benefits, particularly in hypercatabolic mammals, e.g., patients following surgery or undergoing other stress conditions. These transesterification products provide improved overall nutrition and dietary support without elevating cholesterol levels.

Accordingly, an object of the invention is to provide a transesterification composition in the form of a structured lipid which has a variety of nutritional applications.

Another object of the invention is to provide a structured lipid formed of a transesterification product which contains a dairy fat as one its precursors.

A further object of the invention is to provide a method of treating hypercatabolic mammals by nutritional support therapy.

These and other objects and features of the invention will be apparent from the following description.

SUMMARY OF THE INVENTION

The present invention features compositions useful for a variety of nutritional applications and methods of treating hypercatabolic mammals with nutritional therapy. These features of the invention are accomplished by treatment with a structured lipid formed of a transesterification product of a mixture of triglycerides and fattY acids or derivatives or hydrolysis products thereof. The triglycerides and fatty acids forming the pre-transesterification mixture are 10-90% by weight, preferably 20-70% by weight, dairy fat; 0-90% by weight, preferably 10-50% by weight medium-chain triglycerides; and 0-80%, preferably 10-30% by weight long-chain triglycerides, most preferably polyunsaturated triglycerides. A most preferred mixture has about 50% by weight dairy fat, about 35% by weight medium-chain triglycerides, and about 15% by weight polyunsaturated long-chain triglycerides. Another preferred mixture has about 60% by weight dairy fat and 40% by weight medium-chain triglycerides. The long-chain triglycerides (if used) are preferably supplied by oils selected from a group consisting of vegetable oils, marine oils, fruit and seed oils, and their mixtures. The vegetable oils act as a source of ω6 fatty acids, having ω6 as their primary fatty acids, while the marine oils have ω3 fatty acids as a primary constituent. The fruit and seed oils have ω9 oils and/or gamma linolenic acid ("GLA") as a primary constituents.

As noted, the present invention also features a method of treating hypercatabolic mammals, preferably human patients suffering stress following surgery and a variety of other shock-causing conditions, by nutritional support therapy. The nutritional support therapy is carried out by supplying the structured lipid composition of the present invention as the primary fat source in the diet. This type of nutritional support therapy provides unexpected benefits in nitrogen balance, protein formation and protein catabolism rates.

DETAILED DESCRIPTION

The present invention provides formulations and compositions which overcome the drawbacks of conventional dairy fats. The modified dairy fat compositions not only should be preferred for consumer use over conventional dairy products but also can become candidates for enteral and parenteral nutrition and treatment of hospitalized patients.

The invention provides a transesterification product made using standard techniques, e.g., sodium methylate, to obtain a randomly distributed triglyceride. The initial starting material is a mixture of triglycerides, with the possibility of free fatty acids or partially, or totally hydrolyzed triglycerides included. Dairy fats, e.g., butter oil, and medium-chain triglycerides ($C_6$–$C_{12}$, primarily $C_8$ and $C_{10}$) are blended, possibly with polyunsaturated long-chain triglycerides, to form an initial oil or fat "pool." This pool is then transesterified, preferably by a random transesterification method, to form a structured lipid. Varying the ratios of the components of the initial pool will modify the consistency and properties of the composition, e.g., melting point and smoking temperature. If long-chain triglycerides are used in the initial pool, vegetable oils such as soy, corn, safflower or sunflower oil, which are rich in polyunsaturates, can be used to provide the ω6 fatty acids, primarily linoleic acid, necessary for essential fatty acid nutrition. In addition, marine oils such as menhaden, salmon, mackerel and other ω3 rich oils can be used to provide ω3 fatty acids to the final product while fruit and seed oils rich in ω9 fatty acids and GLA, e.g., olive, canola, hybrid safflower or sunflower, borage, black currant and evening primrose oils, can add ω9 fatty acids and/or GLA to the pool. By selecting the proper triglyceride ratios and mix, the benefits of each type triglyceride can be obtained from the structured lipid and total fatty nutrition can be supplied. The following Examples will more clearly illustrate the present invention.

EXAMPLE 1

In this Example, a liquid oil suitable for use as a salad oil, frying oil or for other food applications was made using a random transesterification procedure. The initial fatty acid pool contained a mixture of about 60% dairy fat, specifically deodorized butter oil, and 40% medium-chain triglycerides. Deodorized butter oil is available from a number of sources, while medium-chain triglycerides ($C_6$-$C_{12}$, essentially $C_8$-$C_{10}$) are available from Capitol City Products, Columbus, Ohio, under the trade name Captex 300. Table 1 lists the fattY acid profile for the butter oil, Captex 300 and the transesterification product, a Type I rearranged lipid. Type I lipids have two "parents," dairy fats and medium-chain triglycerides, while Type II lipids start from a mixture of dairy fats, medium-chain triglycerides and long-chain triglycerides. Type I lipids have altered physical and chemical properties, e.g., they are softer and more fluid, while enhancing their rate of absorption and oxidation because of the MCT acids.

TABLE 1

|  | Butter Oil | MCT | Type I Dairy Fat |
|---|---|---|---|
| C6:0 | 1.8 | 0.1 | 0.5 |
| C8:0 | 1.3 | 67.3 | 23.7 |
| C10:0 | 3.2 | 29.3 | 13.1 |
| C12:0 | 3.7 | 0.4 | 2.5 |
| C14:0 | 11.4 | 0.1 | 7.4 |
| C16:0 | 28.6 | 0.1 | 19.0 |
| C18:0 | 10.8 | 0.0 | 7.1 |
| C18:1 | 24.2 | 0.2 | 16.1 |
| C18:2 | 3.4 | 0.2 | 2.3 |
| C18:3 | 0.6 | 0.0 | 0.3 |
| Others | 11.0 | 2.3 | 8.0 |

As noted, this transesterified product is a liquid suitable for a variety of food uses. This product also may be used for enteral or parenteral nutrition for hospitalized patients if other essential minerals, amino acids, and fatty acids are added.

EXAMPLE 2

In this Example, a more complex starting mixture is used to form the structured lipid. The pre-transesterification mixture contains approximately 50% deodorized butter oil, 35% medium-chain triglycerides (Captex 300), and 15% deodorized sunflower oil. Table 2 gives the fatty acid profile for each of the premixture components and for the randomly transesterified product, a Type II dairy fat.

TABLE 2

|  | Butter Oil | MCT | Sunflower Oil | Type II Modified Fat |
|---|---|---|---|---|
| C6:0 | 1.6 | 0.1 | 0.0 | 0.8 |
| C8:0 | 1.3 | 64.0 | 0.0 | 22.0 |
| C10:0 | 3.0 | 35.6 | 0.0 | 12.9 |
| C12:0 | 3.5 | 0.3 | 0.0 | 2.3 |
| C14:0 | 11.8 | 0.0 | 0.1 | 6.2 |
| C16:0 | 31.3 | 0.0 | 7.6 | 17.3 |
| C18:0 | 10.9 | 0.0 | 4.2 | 6.3 |
| C18:1 | 25.9 | 0.0 | 22.3 | 16.3 |
| C18:2 | 2.5 | 0.0 | 63.8 | 12.9 |
| C18:3 | 1.0 | 0.0 | 0.9 | 0.6 |
| Others | 7.2 | — | 1.1 | 2.4 |

Because the sunflower oil has a high linoleic acid (C18:2) concentration, this modified dairy fat provides sufficient essential fatty acids to be used as a total fat supplement for parenteral or enteral nutrition use. At room temperature, this product has a very soft plastic consistency and is also suitable for use in ford products as spreads, confectionary uses, bakery goods, and other near-oil uses. Upon emulsification with water, essential amino acids and minerals, and an emulsifier, this structure could be used for a variety of nutritional support applications.

EXAMPLE 3

In this Example, burned rats were used in a feeding experiment to determine the efficacy of the Type II dairy fat described in Example 2 as a nutritional source for hypercatabolic mammals. The dairy fat was emulsified and amino acids and minerals are added for a complete diet. Table 3 shows the composition of the diet.

TABLE 3

| Composition of Enteral Diets - 250 kcal/kg day | | | |
|---|---|---|---|
|  | Group I (AA, Dextrose and LCT*) | Group II (AA, Dextrose and MCT**) | Group III (AA, Dextrose and Structured Lipid) |
| amino acids (g/liter) | 39.0 | 39.0 | 39.0 |
| dextrose (g/liter) 148.2 | 148.2 | 148.2 |  |
| lipid (g/liter) 37.3 | 37.3 | 37.3 |  |
| Additives |  |  |  |
| sodium chloride (mEq/liter) | 30.0 | 30.0 | 30.0 |
| sodium acetate (mEq/liter) | 30.0 | 30.0 | 30.0 |
| potassium chloride (mEq/liter) | 30.0 | 30.0 | 30.0 |
| potassium acetate (mEq/liter) | 25.0 | 25.0 | 25.0 |
| potassium phosphate (mEq/liter) | 15.0 | 15.0 | 15.0 |
| calcium gluconate (mEq/liter) | 8.0 | 8.0 | 8.0 |
| magnesium sulfate (mEq/liter) | 8.0 | 8.0 | 8.0 |
| trace mineral mix (mEq/liter) | 8.0 | 8.0 | 8.0 |
| choline (mg/liter) 300.0 | 300.0 | 300.0 |  |
| multivitamin mix (ml/liter) | 5.0 | 5.0 | 5.0 |

Rate Received 50 ml/day
*LCT = long-chain triglyceride
*MCT = medium-chain triglyceride The lipid emulsions were fed to rats which had been catheterized to allow continuous infusion and free movement of the rats. The rats then received a full thickness scald burn injury by immersing 25% of their body surface in boiling water for 15 seconds. The experimental protocol is further described in U.S. Pat. No. 4,528,197 at column 3, line 30 et seq.

The burned and surgically treated rats were divided into three groups, each receiving the same diet except for the identity of the lipid. The first group received soybean oil (LCT), a second group received medium-chain triglycerides (MCT Captex 300), and a third group received the structured triglyceride as the lipid in the diet. All groups were feed the same amount of calories, protein, dextrose and lipid. The compositions of the enteral dose, as shown in Table 3, were identical, except for the identifY of the lipid. All of the rats survived three days on the enteral feeding.

TABLE 4

Effect of thermal injury on body weight and nitrogen balance in rats during enteral feeding (250 kcal/kg day).

|  | n | Initial body weight (g) | Final body weight (g) | Weight loss (g/3 days) | Cumulative* nitrogen balance (mgN/48 hr) |
|---|---|---|---|---|---|
| Group I (AA, Dextrose and LCT) | 10 | 201.5 ± 2.7 | 186.6 ± 2.8 | 14.9 ± 1.5 | −12.3 ± 9.3 |
| Group II (AA, Dextrose and MCT) | 8 | 202.9 ± 2.1 | 187.8 ± 2.3 | 15.1 ± 1.2 | −28.6 ± 19.8 |
| Group III (AA, Dextrose and Structured Lipid) | 8 | 195.6 ± 2.7 | 186.0 ± 2.1 | 9.6 + 1.9** | +41.2 ± 13.9** |

Values are Means ± SEM
n = number of rats
*Cumulative nitrogen balance calculated from day 1 and 2 postsurgery and burn
**p < 0.05, Group III vs. Groups I and II Table 4 sets forth the effect of diet and thermal injury on body weight change and nitrogen metabolic balance in rats. Nitrogen balance was calculated based on total urinary nitrogen excretion and calculated nitrogen input. The nitrogen in the urine was detected using a spectrophotometer by measuring the change.

The group receiving the structured lipid had significantly less weight loss in the three day period and had a significantly positive nitrogen balance after 48 hours. This is in contrast to the negative nitrogen balance of the other two groups. A positive nitrogen balance is an indication that a new protein is being made, not just catabolized to provide energy. This positive nitrogen balance is unexpected and shows an increase in protein formation by feeding a diet rich in lipid rather than protein.

TABLE 5

Effect of thermal injury on respiratory quotient (RQ), oxygen consumption and estimated energy expenditure in rats during enteral feeding (250 kcal/kg day).

|  | n | RQ | Oxygen Consumption (uMol/100 g hr) | Estimated Energy Expenditure (kcal/kg day) |
|---|---|---|---|---|
| Group I (AA, Dextrose and LCT) | 10 | 1.02 ± 0.01 | 4973 ± 312 | 134.2 ± 8.3 |
| Group II (AA, Dextrose and MCT) | 8 | 1.00 ± 0.01 | 4856 ± 287 | 130.2 ± 7.7 |
| Group III (AA, Dextrose and Structured Lipid) | 8 | 1.01 ± 0.01 | 5983 ± 169* | 161.1 ± 4.7* |

Values are Means ± SEM
n = number of rats
* = p < 0.05, Group III vs. Groups I and II Table 5 shows the effect of diet on the respiratory quotient (RQ), oxygen consumption and estimate energy expenditures for the three groups on animals. Although the respiratory quotients are substantially equal, there is a statistically significant difference between the oxygen consumption and energy expenditure of the rats fed the structured lipid diet. This surprising result may indicate that the rats are recovering sooner from the hypercatabolic shock if fed the structured lipid diet.

TABLE 6

Liver weight, liver and muscle protein percent and serum albumin concentration.

|  | Liver Protein (%) | Muscle Protein (%) | Serum Albumin (g/dl) |
|---|---|---|---|
| Group I (AA, Dextrose and LCT) | 18.5 ± 0.11 | 17.9 ± 0.4 | 2.17 ± 0.13 |
| Group II (AA, Dextrose and MCT) | 18.6 ± 0.3 | 17.9 ± 0.6 | 2.94 ± 0.04 |
| Group III (AA, Dextrose and Structured Lipid) | 20.3 ± 0.6* | 18.4 ± 0.7 | 2.75 ± 0.14** |

Values are Means ± SEM
n = number of rats
* = p < 0.05, Group III vs. Groups I and II
** - p < 0.05, Group III vs. Group I Table 6 contrasts the percent protein liver and muscle as well as the circulating serum albumin levels for the three groups of rats. There is no significant difference in muscle protein percentage among the three groups but the rats fed the structured lipid diet have a significantly higher liver protein content than the other two groups. In addition, the circulating serum albumin levels for the rats fed the structured lipid is significantly higher than that for the rats fed the long-chain triglyceride diet. Although the rats fed the MCT diet have an even higher circulating serum albumin level then the structured lipid diet rats, this difference is not statistically significant.

TABLE 7

Muscle and liver protein synthesis (uMol leucine/g day) and fractional synthetic rates (FSR).

| Diet | n | Muscle | | Liver | |
|---|---|---|---|---|---|
| | | Protein synthesis | FSR (%/day) | Protein synthesis | FSR (%/day) |
| Group I (AA, Dextrose and LCT) | 9 | 2.7 ± 0.2 | 2.4 ± 0.1 | 41.4 ± 4.3 | 31.1 ± 3.4 |
| Group II (AA, Dextrose and MCT) | 8 | 2.9 ± 0.1 | 2.6 ± 0.1 | 38.8 ± 2.5 | 28.8 ± 1.7 |
| Group III (AA, Dextrose and Structured Lipid) | 8 | 3.7 ± 0.3* | 3.2 ± 0.3* | 76.4 ± 5.0* | 51.9 ± 2.5* |

Values are Means ± SEM
n = number of rats
* = $P < 0.05$, Group III vs. Group I and II Table 7 illustrates the muscle and liver protein synthesis level and fractional synthetic rates for rats after three days of feeding with the lipid-based emulsion diets. A $C^{14}$leucine-tracer was included as part of the amino acids and the amount of leucine in breath and plasma was measured. The fractional synthetic rate, which was calculated using the equation of Garlick: et al., and the protein synthesis level are both measures of incorporation of the radioactively labeled leucine into muscle and liver tissue. The rats fed the structured lipid composition of the present invention had significantly increased protein synthesis and fractional synthetic rates in both muscle and liver. This finding shows that the structured lipid was superior at reducing whole body protein catabolism and stimulating muscle and liver protein anabolism than either LCT or MCT diets.

These findings are significant in terms of treating stressed patients, e.g., those having undergone recent surgery, or suffering from cancer or disease-caused malnutrition. The nutritional benefits, increasing synthesis rates of protein in both muscle and liver solely by a change in the type of lipid source, is unexpected and surprising. In fact, other structured lipids have not shown as positive an effect on protein formation as does the dairy fat structured lipid.

EXAMPLE 4

In this Example, a soft, plastic fat suitable for the preparations of margarines, frying fats, bakery shortenings, and other food uses has made using a random transesterification procedure. The initial fatty acid pool contained a mixture of about 80% deodorized butter oil and 20% sunflower oil which has a high percentage of polyunsaturated long-chain triglycerides. Table 8 lists the fatty acid profile for the butter oil, sunflower, and transesterification product, a Type III rearranged lipid. The Type III lipids have dairy fat as their main constituent and long-chain triglycerides, preferably polyunsaturated long-chain triglycerides, a the other constituent in the pre-reaction pool.

TABLE 8

| | Butter Oil | Sunflower Oil | Type III Modified Dairy Fat |
|---|---|---|---|
| C6:0 | 1.8 | 0.0 | 1.5 |
| C8:0 | 1.3 | 0.0 | 1.0 |
| C10:0 | 3.2 | 0.0 | 2.5 |
| C12:0 | 3.7 | 0.0 | 2.9 |
| C14:0 | 11.4 | 0.1 | 9.0 |
| C16:0 | 28.6 | 6.8 | 24.2 |
| C18:0 | 10.8 | 4.0 | 9.4 |
| C18:1 | 24.2 | 20.0 | 23.4 |
| C18:2 | 3.4 | 66.1 | 16.4 |
| C18:3 | 0.6 | 1.6 | 1.4 |
| Others | 11.0 | 1.4 | 8.3 |

The Type III modified dairy fat obtained by the transesterification procedure is, as noted, suitable for a number of food uses. This product is easily modified to contain sufficient linoleic acid to satisfy the essential fatty acid nutrition while yielding a consistency that is easily modifiable by selection of the initial fat pool.

The foregoing Examples were meant to be purely illustrative and not limiting. Those skilled in the art will realize that modifications and other formulations then those shown in the Examples may be used in the present invention. The following claims, rather than the Examples, therefore define the invention.

What is claimed is:

1. A composition useful for nutritional applications comprising a structured lipid formed as a transesterification product of a mixture consisting essentially of 10–90% by weight dairy fat, 10–50% by weight additional medium-chain triglycerides and 0–80% by weight additional long-chain triglycerides, or hydrolysis products thereof.

2. The composition of claim 1 wherein said dairy fat comprises 20–70% by weight of said mixture.

3. The composition of claim 1 wherein said additional long-chain triglycerides comprise 10–30% by weight of said mixture.

4. The composition of claim 1 wherein said additional long-chain triglycerides comprises polyunsaturated long-chain triglycerides.

5. The composition of claim 1 wherein said mixture consists essentially of 20–70% by weight dairy fat, 10–50% by weight additional medium-chain triglycerides, and 10–30% by weight additional polyunsaturated long-chain triglycerides, or hydrolysis products thereof.

6. The composition of claim 5 wherein said mixture consists essentially of about 50% by weight dairy fat, about 35% by weight additional medium-chain triglycerides, and about 15% by weight additional polyunsaturated long-chain triglycerides, or hydrolysis products thereof.

7. The composition of claim 4 wherein said mixture consists essentially of about 20–80% by weight dairy fat and about 20–50% by weight additional polyunsaturated long-chain triglycerides, or hydrolysis products thereto.

8. The composition of claim 1 wherein said additional long-chain triglycerides are in the form of oils selected from a group consisting of vegetable oils, marine oils, fruit and seed oils, and mixtures thereof.

9. The composition of claim 8 wherein said vegetable oils are selected from oils having $\omega 6$ fatty acids as their primary fatty acids.

10. The composition of claim 8 wherein said marine oils are selected from oils having $\omega 3$ fatty acids as their primary fatty acids.

11. The composition of claim 8 wherein said fruit and seed oils are selected from the group of fruit and seed oils having $\omega 9$ fatty acids and gamma linolenic acid as their primary fatty acids.

12. The composition of claim 1 wherein said mixture consists essentially of about 60% by weight dairy fat and about 40% by weight additional medium-chain triglycerides, or hydrolysis products thereof.

13. A method of treating hypercatabolic mammals by nutritional support therapy comprising the step of supplying a structured lipid as the primary fat source in said therapy, said structured lipid formed as a transesterification product of a mixture consisting essentially of 10–90% by weight dairy fat, 10–50% by weight additional medium-chain triglycerides and 0–80% by weight additional long-chain triglycerides, or hydrolysis products thereof.

14. The method of claim 13 wherein said dairy fat comprises 20–70% by weight of said mixture.

15. The method of claim 13 wherein said additional long-chain triglycerides comprise 10–30% by weight of said mixture before transesterification.

16. The method of claim 13 wherein said additional long-chain triglyceride comprises polyunsaturated long-chain triglycerides.

17. The method of claim 13 wherein said mixture consists essentially of 20–70% by weight dairy fat, 10–50% by additional weight medium-chain triglycerides, and 10–30% by weight additional polyunsaturated long-chain triglycerides, or hydrolysis products thereof.

18. The method of claim 13 wherein said additional long-chain triglycerides are in the form of oils selected from a group consisting of vegetable oils, marine oils, fruit and seed oils, and mixtures thereof.

19. The method of claim 13 wherein said mixture consists essentially of about 60% by weight dairy fat and about 40% by weight additional medium-chain triglycerides, or hydrolysis products thereof.

20. The method of claim 13 wherein said hypercatabolic mammals comprise human patients.

* * * * *